United States Patent [19]

Burke et al.

[11] Patent Number: 5,001,257

[45] Date of Patent: Mar. 19, 1991

[54] PREPARATION OF 4-PENTENOIC ACID, AMIDE OR ESTERS BY ISOMERIZATION

[75] Inventors: Patrick M. Burke; Francis J. Waller, both of Wilmington, Del.

[73] Assignee: E. I. Du Pont de Nemours and Company, Wilmington, Del.

[21] Appl. No.: 48,651

[22] Filed: May 11, 1987

[51] Int. Cl.$^5$ .................. C07C 51/353; C07C 67/333; C07C 69/533

[52] U.S. Cl. .................................... 560/205; 562/598; 564/204

[58] Field of Search ........................ 560/205; 562/598; 564/204

[56] References Cited

U.S. PATENT DOCUMENTS 3,282,875 11/1966 Connolly et al. ............... 526/247 X
4,529,815 7/1985 Schneider et al. .................. 560/205

*Primary Examiner*—Vivian Garner

[57] ABSTRACT

Perfluorinated acid ion-exchange resins are highly effective catalysts for the isomerization of 3-pentenoic compounds to 4-pentenoic compounds, especially if the catalysts contain a group 8 metal in an oxidation state of at least +2.

6 Claims, No Drawings

PREPARATION OF 4-PENTENOIC ACID, AMIDE OR ESTERS BY ISOMERIZATION

FIELD OF THE INVENTION

This invention relates to the selective isomerization of 3-pentenoic acid, amide or esters, to form the corresponding 4-pentenoic acid, amide or esters, by the use of perfluorinated ion-exchange polymer catalysts, sometimes hereinafter referred to as "PFIEP" catalysts.

BACKGROUND OF THE INVENTION

Schneider et al. U.S. Pat. No. 4,529,815 discloses the preparation of 4-pentenoates by the isomerization at elevated temperatures of 3-pentenoates using an acidic-ion-exchange resin containing a noble metal of group 8 of the periodic table as the catalyst.

Perfluorinated ion-exchange polymers are commercially available as Nafion ®. The preparation of such products is disclosed in U.S. Pat. No. 3,282,875 to Connolly et al.

Perfluorinated ion-exchange polymers have been previously employed as isomerization catalysts—see, for example, U.S. Pat. No. 4,022,847 and 4,038,213 to McClure and McClure et al. which disclose the isomerization of alkanes.

SUMMARY OF THE INVENTION

The present invention is a process for the preparation of 4-pentenoic acid, amide or esters, i.e., a compound having the formula

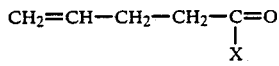

where X is OH, NH$_2$, or OR and R is alkyl of 1-8 carbon atoms, by the isomerization of a corresponding 3-pentenoic acid, amide or ester, i.e., a compound having the formula

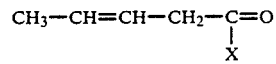

where X is OH, NH$_2$ or OR and R is alkyl of 1-8 carbon atoms, with a perfluorinated ion-exchange polymer catalyst, at an elevated temperature.

In a preferred embodiment the perfluorinated acid ion-exchange polymer catalyst contains at least one noble metal of group 8 of the periodic table in an oxidation state of at least +2 as a promoter. The preferred noble metals are rhodium, platinum and palladium. It is preferable to have the noble metal present in the amount of 0.1 to 4% by weight of the catalyst.

The process of the present invention is particularly effective in the isomerization of methyl-3-pentenoate to methyl-4-pentenoate.

DETAILED DESCRIPTION

The perfluorinated acid ion-exchange polymer catalyst used in the present invention is prepared from a suitable perfluorinated acid ion-exchange polymer. Such a polymer is a perfluorinated sulfonic acid polymer (PFIEP [SO$_3$H]), or a blend of perfluorinated sulfonic acid and perfluorinated carboxylic acid resins (PFIEP [SO$_3$H]/PFIEP [CO$_2$H]). Most preferred perfluorinated sulfonic acid polymers have a number average molecular weight of at least about 5000. Preferably, the PFIEP contains a sufficient number of sulfonic acid groups to give an equivalent weight of from about 500 to about 2000, and most preferably from about 700 to about 1500. The equivalent weight, E.W., is determined by the formula:

E.W. = M.W./number of acid groups, where M.W. is the molecular weight of the perfluorocarbon polymer.

Although the polymer backbone will largely comprise perfluorinated carbon atoms, it is not necessary that all other atoms be excluded. For example, ether oxygen may be present in the backbone or in the side chains of the polymer. Other atoms or groups such as hydrogen, chlorine and carboxyl groups may be present in limited amounts without significantly affecting the stability or operability of the polymer under the process conditions. It is preferred that the polymer contain no greater than about 5 weight percent total of such other atoms or groups.

The perfluorinated acid ion-exchange polymer may be a blend of two or more ion-exchange polymers. The preparation of blends of perfluorinated sulfonic acid and perfluorinated carboxylic acid polymers is disclosed in U.S. Pat. No. 4,176,215, the disclosure of which is incorporated herein by reference. Preferred blends of perfluorinated sulfonic acid and perfluorinated carboxylic acid polymers include blends of tetrafluoroethylene copolymers with methylperfluoro-5-methyl-4,7-dioxanon-8-eneoate and tetrafluoroethylene copolymers with perfluoro-(3,6-dioxa-4-methyl-7-octene) sulfonic acid. Most preferred blends have an ion-exchange capacity of at least 0.7 meq/g. Preferably, the weight ratio of sulfonic acid polymer to carboxylic acid polymer in the blend is from about 1:1 to about 10:1.

The perfluorinated acid ion-exchange polymer is ground to small particles—usually 20 to 200 mesh size and employed as catalyst, but improved results are obtained if the perfluorinated acid ion-exchange polymer is subjected to an exchange with a salt of a noble metal of group 8 of the periodic table whereby an amount by weight of the catalyst of between about 0.1 to 4% of the noble metal is incorporated into the perfluorinated acid ion-exchange polymer. The noble metal is preferably present in the oxidation state of at least +2. The noble metal acts to promote the reaction.

The process of the invention is carried out at elevated temperatures. The isomerization reaction proceeds faster at higher temperatures, but the catalyst is destroyed faster at high temperatures; therefore, some compromises must be made to obtain high yield in a relatively short reaction time without destroying the catalyst. A suitable reaction temperature is preferably in the range of 120° to 200° C.

The use of the perfluorinated acid ion-exchange polymer catalyst is substantially more effective (i.e., it has a higher turnover rate) than the acid-ion-exchange polymers used in the art, and is more selective in the conversion of the 3-pentenoic compound to the 4-pentenoic compound rather than to the 2-pentenoic compound. Turnover rate (TR) is defined as the number of moles of the 4-pentenoic compound formed per mole of group 8 metal in the catalyst per hour. Selectivity is defined as the number of moles of the 4-pentenoic compound formed, divided by the number of moles of 2-pentenoic compound formed during the isomerization reaction. In making this latter calculation the number of moles of 2-pentenoic compound present in the starting mixture containing the 3-pentenoic compound is not considered.

The catalyst may be used in a variety of forms including beads, powders, tubes, films, and coatings on support materials. Suitable substrates include alumina, silica, porous glass, etc. Supported catalysts of this type are known in the art—see U.S. Pat. No. 4,035,213.

It is not necessary that the feed stream be pure 3-pentenoic compound; diluents may be present so long as they do not interfere with the catalyst, the 3-pentenoic compound or the 4-pentenoic compound formed. Such diluents could be benzonitrile, o-xylene, hexadecane and tetramethylenesulfone.

In the following examples which illustrate the invention and compare the invention to the art, all parts and percentages are in parts by weight, and all temperatures are in degrees centigrade.

EXAMPLE 1A

Six grams of Nafion ® Superacid Catalyst Type NR50, a commercially available perfluorinated acid ion-exchange polymer having an ion-exchanging capacity of at least 0.8 meq/g, was ground to a particle size of less than 100 mesh, and stirred in a solution containing 0.2 g (0.75 m mole) platinum chloride ($PtCl_2$) in a mixture of 50 ml of acetonitrile and 100 ml of distilled water. This ion-exchange polymer is in the hydrolyzed acid form, and is prepared from a copolymer of tetrafluoroethylene and perfluoro-3,6-dioxa-4-methyl-7-octene sulfonyl fluoride. It has a bulk density of approximately 1, and a surface area ($m^2/g$) of approximately 0.02. After heating at 80° C. for 4 hours the exchanged resin was filtered, washed with 100 ml of distilled water and dried in a vacuum oven at 100° C. under $N_2$ for 3 hours. The dried resin weighed 6.24 g. Analysis showed 1.56% platinum. Ten grams of a mixture containing 99% trans-methyl-3-pentenoate (tM3P) and 1% methyl-2-pentenoate (M2P) was heated to reflux (135°) under $N_2$. One gram of the platinum-exchanged catalyst was rapidly added and the resulting slurry was maintained at 135° C. with stirring. Samples (0.1 ml) were taken after 1, 5 and 30 minutes. Aliquots (5 μl) were diluted in 2ml methanol containing 5 mg o-dichlorobenzene (internal gas chromatographic standard) and analyzed. The following isomer distributions, turnover rates (TR) and selectivities (SEL) were found:

| Time Min. | % M4P | % M3P | % M2P | TR($Hr^{-1}$) (M4P) | SEL (M4P/M2P) |
|---|---|---|---|---|---|
| 1 | 6.2 | 92.0 | 1.8 | 4078 | 7.75 |
| 5 | 8.4 | 88.1 | 3.5 | 1105 | 3.36 |
| 30 | 8.2 | 87.6 | 4.2 | 180 | 2.56 |

The turnover rate (TR) where catalyst contains a metal is defined as the number of moles of M4P formed per mole of noble metal per hour.

The results show an initial turnover rate of 4078 moles M4P per mole Pt per hour and an initial selectivity of 7.75 moles M4P per mole of M2P (cis+trans isomer).

EXAMPLE 1B

The procedure of Example 1A was repeated, except that the catalyst contained 0.24% rhodium in a +3 oxidation state, instead of platinum. Gas Chromatographic analysis of the reaction solutions gave the following results:

| Time Min. | % M4P | % M2P | TR($Hr^{-1}$) (M4P) | SEL (M4P/M2P) |
|---|---|---|---|---|
| 6.5 | 7.4 | 1.7 | 2567 | 10.6 |
| 11.5 | 7.9 | 2.2 | 1549 | 7.2 |
| 31 | 8.3 | 3.5 | 604 | 3.3 |

The results show an initial turnover rate of 2567 moles of M4P per mole of Rh per hour and an initial selectivity of 10.6 moles of M4P per mole of M2P.

CONTROL EXAMPLE A

For comparison with the above, 1g of a polystyrenedivinyl benzene based sulfonic acid resin (Amberlyst 15), exchanged with 1.29% Pd in a +2 oxidation state was used to isomerize a mixture containing 98.8% M3P, and 1.2% M2P. Gas Chromatographic analysis gave the following isomer distributions turnover rates and selectivities:

| Time Min. | % M4P | % M3P | % M2P | TR($Hr^{-1}$) (M4P) | SEL (M4P/M2P) |
|---|---|---|---|---|---|
| 1 | 3.6 | 94.5 | 2.0 | 1562 | 4.5 |
| 5 | 4.3 | 93.9 | 3.5 | 373 | 1.9 |
| 30 | 5.4 | 91.1 | 13.4 | 78 | 0.44 |

These results indicate that the Pd exchanged polystyrenedivinyl benzene catalysts are substantially less active (TR Ratio=1562/4076 or 0.38), and less selective (4.5 vs. 7.5 selectivity), than the catalyst of Example 1A and 1B.

EXAMPLE 2

Solid Acid Catalysts (No group 8 metal)

To 10.0 g of trans-methyl-3-pentenoate (tM3P) containing 0.9% methyl-2-pentenoate (M2P) at 135° C. under nitrogen was added 1.0 g 40-60 mesh, perfluorinated ion-exchange polymer catalyst, in the acid form. Samples were taken at intervals and analyzed by capillary Gas Chromatography. The following isomer distributions were found:

| Time Min. | M4P | M2P | SEL M4P/M2P |
|---|---|---|---|
| 5 | 0.5 | 1.0 | 5 |
| 30 | 2.8 | 2.0 | 2.5 |
| 60 | 4.9 | 3.4 | 2.0 |
| 180 | 7.6 | 9.0 | 0.9 |

The results show that M4P is preferentially formed up to at least 60 minutes contact time.

EXAMPLE 3

Selective isomerization of 3-pentenamide to 4-pentenamide

A solution of trans-3-pentenamide (2.0 g) in isobutyric acid (10 ml) was heated to 130° under nitrogen. A sample of this solution, taken after 1 hour at 130°, showed no 4-pentenamide when analyzed by capillary Gas Chromatograph as its trimethylsilyl derivative.

To the above solution at 130° was added 1.0 g 1.1% platinum in a +2 oxidation state on perfluorinated acid ion-exchange resin catalyst. Samples were taken after 5 and 30 minutes and analyzed by a Gas Chromatograph.

The percentage of each isomer in the mixture is summarized below.

| Catalyst | Time Min. | % 4PNAM | % 2PNAM | 4PNAM/2PNAM |
|---|---|---|---|---|
| 1.1% Pt+2 on PFIEP | 5 | 2.1 | 0.4 | 5.1 |
| | 30 | 6.6 | 2.9 | 2.3 |

EXAMPLE 4

Trans-3-pentenoic acid (10.0 g) was heated to 135° C. under nitrogen. A 5 μl sample taken after 15 minutes at 135° C. showed 0.79% trans-2-pentenoic acid and no 4-pentenoic acid when analyzed by a capillary Gas Chromatograph as the methyl esters. The ester was prepared by heating 5 μl acid, 10 mg p-toluenesulfonic acid and 2 ml methanol to 90° C. for 30 minutes.

To the 10 g 3-pentenoic acid at 135° C. was added 1 g of a 10-35 mesh size polymer blend prepared from a blend of PFIEP, in the sulfonic acid form (75%) and PFIEP in the carboxylic acid form (25%). This blend was exchanged with 0.64% palladium in a +2 oxidation state. Samples taken at intervals and analyzed by capillary Gas Chromatography as the methyl esters as outlined above, showed the following isomer distributions:

| Catalyst | Time Min. | % 4PA** | % 2PA | 4PA/2PA | % Lactone* |
|---|---|---|---|---|---|
| 0.64% Pd+2 on PFIEP [SO3H]/ PFIEP [CO2H] | 0 | 0 | 0.79 | — | 0 |
| | 3 | 0.72 | 1.10 | 2.29 | 5.9 |
| | 5 | 0.94 | 1.47 | 1.37 | 14.5 |
| | 15 | 2.21 | 2.42 | 1.35 | 39.4 |

*lactone = gamma-valerolactone (based on total isomer content)
**the % pentenoic acid does not include lactone The above experiment was repeated except that the catalyst was changed to 1 g of 60-100 mesh size 100% PFIEP in the sulfonic acid form containing 0.55% platinum in a +2 oxidation state. Gas Chromatographic analysis at time intervals gave the following results:

| Catalyst | Time Min. | % 4PA** | % 2PA | 4PA/2PA | % Lactone* |
|---|---|---|---|---|---|
| 0.55% Pt+2 on PFIEP [SO3H] | 0 | 0 | 0.79 | — | 0 |
| | 3 | 0.87 | 1.11 | 2.65 | 12.2 |
| | 5 | 1.74 | 2.5 | 1.01 | 40.1 |
| | 15 | 8.16 | 12.9 | 0.67 | 80.6 |

The results show that 4PA is initially formed preferentially with the Pd, and Pt exchanged resins and blends. Lactone formation increases with time.

EXAMPLE 5

Blends of Perfluorinated Sulfonic Acids and Perfluorinated Carboxylic Acid

Blends of PFIEP is the sulfonic acid form and PFIEP in the carboxylic acid form containing 75%, 66.6% and 50% of the sulfonic acid polymer and a mesh size of 10-35 were exchanged with Pd+2 to a metal content of 0.71, 0.94 and 0.37% Pd respectively. To 10 g tM3P at 135° C. under N2 was added 1.0 g of the exchanged blend. Samples were taken at intervals and analyzed by Gas Chromatography for methyl pentenoate isomers. The following isomer distributions were obtained:

| Catalyst | Time Min. | % M4P | % M2P | M4P/M2P | TR(Hr⁻¹) (M4P) |
|---|---|---|---|---|---|
| 0.71% Pd | 0 | 0.0 | 0.82 | — | — |
| | 1 | 0.73 | 0.77 | — | 575 |
| | 5 | 1.26 | 1.62 | 1.7 | 214 |
| | 30 | 3.26 | 2.04 | 2.68 | 86 |
| 0.94% Pd | 1 | 2.17 | 0.94 | 18.0 | 1292 |
| | 5 | 3.45 | 1.60 | 4.4 | 410 |
| | 30 | 5.12 | 3.59 | 1.85 | 102 |
| 0.37% Pd | 1 | 3.19 | 1.15 | 10.63 | 4825 |
| | 5 | 3.79 | 1.48 | 5.76 | 1147 |
| | 30 | 4.70 | 2.33 | 3.11 | 237 |

The data show the result that the blend containing only 50% PFIEP [SO3H] has the highest activity on a catalyst weight basis. Based on metal turnover rate (moles M4P/mole Pd/Hr) this catalyst is 4825/575 (8.4) times more active than the 75% PFIEP [[SO3H] content blend.

EXAMPLE 6

M3P to M4P Isomerization in Solvent Media

A solution of 2.0 g tM3P in 8.0 g of solvent was heated to 135° C. under nitrogen. To this solution at 135° C. was added 1.0 g of a 1.36% Pd on perfluorinated sulfonic acid ion-exchange polymer catalyst. Samples were taken at 1 and 5 minutes and analyzed by Gas Chromatography. The amount of M4P (calculated as a percentage of the total methyl pentenoate isomers present) and the selectivity (% M4P/% M2P formed) for a variety of solvents is summarized below.

| Solvent | 1 Minute % M4P | 1 Minute Sel | 5 Minutes % M4P | 5 Minutes Sel |
|---|---|---|---|---|
| Isobutyric Acid* | 3.48 | 2.09 | 4.72 | 0.63 |
| Dimethyl Adipate | 2.33 | 1.56 | 4.54 | 1.03 |
| Tetramethylenesulfone | 2.58 | 1.16 | 4.54 | 1.27 |
| Benzonitrile | 3.89 | 0.63 | 5.11 | 0.63 |
| o-xylene | 5.36 | 2.17 | 6.72 | 1.74 |
| 1,2,4-trimethylbenzene | 3.18 | 1.90 | 5.83 | 1.31 |
| Hexadecane | 2.17 | 2.0 | 4.98 | 1.73 |

*Gamma-valerolactone formed by ester interchange is a major co-product in carboxylic acid solvents.

The results show that the isomerization can be carried out with both polar and non-polar solvents as diluents.

We claim:

1. A process for the preparation of a compound having the formula

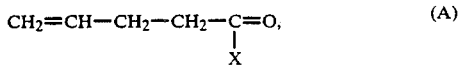

$$CH_2=CH-CH_2-CH_2-\underset{X}{C}=O, \quad (A)$$

where X is OH, NH2, or OR, and R is alkyl of 1-8 carbon atoms, which comprises isomerizing a compound of the formula (B)

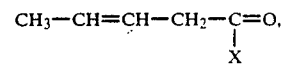

$$CH_3-CH=CH-CH_2-\underset{X}{C}=O,$$

were X is OH, NH2, or OR and R is an alkyl group of 1-8 carbon atoms, by contacting at elevated temperature at least one compound of the formula (B) with a perfluorinated acid ion-exchange resin catalyst containing a noble metal of group 8 of the periodic table in an oxidation state of at least +2, as a promoter.

2. The process of claim 1 in which the noble metal is rhodium, platinum or palladium.

3. The process of claim 1 in which the compound having the formula (B) is methyl-3-pentenoate.

4. The process of claim 1 in which the noble metal is present in the amount of 0.1 to 4% by weight of the catalyst.

5. The process of claim 1 in which the perfluorinated acid ion-exchange resin catalyst is a blend of perfluorinated sulfonic acid polymer and perfluorinated carboxylic acid polymer.

6. The process of claim 5 in which the blend has a weight ratio of sulfonic acid polymer to carboxylic acid polymer of from about 1:1 to 10:1.

* * * * *